US012758168B2

(12) United States Patent
Roser et al.

(10) Patent No.: US 12,758,168 B2
(45) Date of Patent: Oct. 13, 2026

(54) METHOD FOR OPERATING AN IMAGING X-RAY FACILITY AND IMAGING X-RAY FACILITY

(71) Applicant: Siemens Healthineers AG, Forchheim (DE)

(72) Inventors: Philipp Roser, Erlangen (DE); Marcus Pfister, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 154 days.

(21) Appl. No.: 18/931,712

(22) Filed: Oct. 30, 2024

(65) Prior Publication Data

US 2025/0152113 A1 May 15, 2025

(30) Foreign Application Priority Data

Nov. 14, 2023 (DE) ..................... 10 2023 211 326.0

(51) Int. Cl.
*A61B 6/10* (2006.01)
*A61B 6/00* (2006.01)
*A61B 6/08* (2006.01)

(52) U.S. Cl.
CPC ................ *A61B 6/107* (2013.01); *A61B 6/08* (2013.01); *A61B 6/54* (2013.01)

(58) Field of Classification Search
None
See application file for complete search history.

(56) References Cited

U.S. PATENT DOCUMENTS 6,435,717 B1 * 8/2002 Kohler ................... A61B 6/107 378/205
7,767,990 B2 * 8/2010 Cadwalader ......... A61B 6/4423 128/853
8,552,858 B2 * 10/2013 Hohmann ............ A61N 5/1048 600/407

(Continued)

FOREIGN PATENT DOCUMENTS

DE 102014215448 B3 * 12/2015 ............. A61B 6/102
DE 102014218282 A1 3/2016

(Continued)

OTHER PUBLICATIONS

RadioSurfVet "Depth of Field and Light Sight" Vetsuisse Faculty Bern and Zurich—obtained on Sep. 5, 2023. pp. 1-4 with machine translation. https://vetsuisse.com/vet-iml/lernmodule/htmls/slide.html?radiosurfvet%7Cradgeneral%7Ctechnics%7Croentgentube%7C10.

*Primary Examiner* — Thomas R Artman
(74) *Attorney, Agent, or Firm* — Lempia Summerfield Katz LLC

(57) ABSTRACT

A method for operating an imaging X-ray facility is provided. The X-ray facility has an X-ray tube assembly for emitting an X-ray field, with which a fan of light facility for emitting a fan of light, whose extent matches that of the X-ray field, is associated. The method includes covering, by a covering device, an examination object to be exposed to the X-ray field for imaging, for ascertaining and/or representing a distribution of scattered radiation produced by the X-ray field. The method further includes activating the fan of light facility, wherein the covering device at least partially diffusely reflects light of the fan of light on a side of the covering device facing the X-ray tube assembly.

17 Claims, 4 Drawing Sheets

(56) References Cited

U.S. PATENT DOCUMENTS

| | | | | |
|---|---|---|---|---|
| 9,179,886 | B2 * | 11/2015 | Stagnitto | A61B 6/08 |
| 9,820,702 | B2 * | 11/2017 | Osherov | A61B 6/548 |
| 10,556,128 | B2 * | 2/2020 | Weidner | A61B 6/06 |
| 11,191,496 | B2 * | 12/2021 | Chakrabarti | A61B 6/107 |
| 12,279,899 | B2 * | 4/2025 | Foster | G21F 3/00 |
| 2008/0164425 | A1 * | 7/2008 | Cadwalader | A61B 6/107 250/492.1 |
| 2010/0127859 | A1 | 5/2010 | Hohmann et al. | |
| 2014/0029720 | A1 * | 1/2014 | Osherov | A61B 6/107 250/519.1 |
| 2015/0049863 | A1 * | 2/2015 | Stagnitto | A61B 6/08 378/205 |
| 2016/0029980 | A1 * | 2/2016 | Osherov | A61B 6/10 250/519.1 |
| 2019/0038917 | A1 * | 2/2019 | Weidner | A61B 6/06 |
| 2020/0187877 | A1 | 6/2020 | Chakrabarti | |
| 2022/0218295 | A1 * | 7/2022 | Foster | G21F 3/00 |
| 2024/0180506 | A1 * | 6/2024 | Nukui | A61B 6/0407 |
| 2025/0152113 | A1 * | 5/2025 | Roser | A61B 6/107 |

FOREIGN PATENT DOCUMENTS

| | | | |
|---|---|---|---|
| EP | 2117649 | B1 | 10/2012 |
| EP | 3644859 | B1 | 8/2021 |

* cited by examiner

1 - X-ray facility
2 - X-ray tube assembly arrangement
3 - X-ray tube assembly
4 - X-ray detector
5 - C-arm
6 - Beamforming facility
7 - Fan of light facility
8 - Rotating anode
9 - X-ray field
10 - Collimator
11 - Exit window
12 - Mask
13 - Light source
14 - Transparent mirror
15 - Fan of light
21 - Light sensor
22 - Light sensor
23 - Control facility 2 - X-ray tube assembly arrangement
15 - Fan of light
16 - Covering device
17 - Patient
18 - Illuminated region
19 - Individual
20 - Scattered radiation
21 - Light sensor
22 - Light sensor
24 - Radiation protection equipment
25 - Radiation protection screen 16 - Covering device
23 - Control facility
26 - Recording unit
27 - Adjusting unit
28 - Control unit
29 - Evaluation unit
30 - Storage device
31 - Pattern of diffusely reflective partial areas

METHOD FOR OPERATING AN IMAGING X-RAY FACILITY AND IMAGING X-RAY FACILITY

The present patent document claims the benefit of German Patent Application No. 10 2023 211 326.0, filed Nov. 14, 2023, which is hereby incorporated by reference in its entirety.

TECHNICAL FIELD

The disclosure relates to a method for operating an imaging X-ray facility having an X-ray tube assembly for emitting an X-ray field and a fan of light facility for emitting a fan of light, whose extent matches that of the X-ray field. In addition, the disclosure relates to an imaging X-ray facility.

BACKGROUND

In X-ray facilities, (e.g., in medical engineering), X-ray radiation is used that may have an ionizing effect. Therefore, the X-ray field, which is used for the imaging examination, is conventionally limited in its extent to the minimum in order not to stress the patient unnecessarily. Suitable beam-forming facilities are known for this purpose, such as collimator facilities and/or other masking facilities.

To be able to visually follow the extent of the X-ray field, it has already been proposed in the prior art that fan of light facilities are associated with the X-ray tube assembly. In this connection, an X-ray-permeable mirror is introduced into the beam path on the X-ray tube assembly side, and this laterally deflects light irradiated onto it in the direction of the X-rays and may thus provide a fan of light that is congruent with the X-ray field. This optically displays the extent of the X-ray field on the examination object.

Such a fan of light is not a fan because a fan has a two-dimensional extent, but the X-ray is conical or pyramidal in its basic form. Therefore, such a fan of light has the form of a cone or truncated cone or a pyramid or a truncated pyramid. For the sake of simplicity, the term “fan of light” shall nevertheless be used here and below, however.

Because relevant scattered radiation may also occur in X-ray examinations, the staff in the environment of the X-ray facility also need to be protected because the scattered radiation constitutes a serious danger. In fact, a large part of the scattered radiation is released from the examination object, in particular the patient.

Because X-ray radiation is not visible to the human eye, it is challenging for the staff to take adequate protective measures at any instant. The focus of the staff during imaging X-ray examinations is on the care of the patient. Because scattered radiation does not have an immediate short-term adverse effect, scattered radiation protection frequently moves into the background.

It is known in the prior art to use radiation protection equipment, (e.g., radiation protection screens or other shielding components), during the imaging examination with the X-ray facility, (e.g., when staff remain in the space owing to a medical intervention), which equipment has to be matched to the current setting of the X-ray facility, however. This applies, in particular, when a plurality of orientations of the X-ray field is possible, as are given in X-ray facilities with recording arrangements, including an X-ray tube assembly and an X-ray detector, which may be adjusted in many degrees of freedom in the space. One example of this is an X-ray facility with a C-arm, as is frequently used in an angiography system. In certain cases, radiation protection, (e.g., made of lead), adequately positioned for anterior-posterior projections may not necessarily offer equally suitable scattered radiation protection for lateral projections.

To solve this problem, it is known to carry out regular training courses and exercises for the staff, which, however, do not necessarily show the desired result. In particular, their success is highly dependent on individual compliance.

Furthermore, it has been proposed in the prior art that the distribution of scattered radiation is calculated by laborious computing procedures by a computing facility and to display the result to the staff, for example, on a monitor. Owing to the necessary calculations, this variant is time-consuming and expensive, and it is difficult to associate the displayed results with actual protective measures.

SUMMARY AND DESCRIPTION

The disclosure is therefore based on the object of disclosing a possibility for low-effort, time-efficient, intuitively understandable, and/or automatically achievable, adequate adjustment of scattered radiation protective measures.

In order to achieve this object, a method and an X-ray facility are provided. The scope of the present disclosure is defined solely by the appended claims and is not affected to any degree by the statements within this summary. The present embodiments may obviate one or more of the drawbacks or limitations in the related art.

In a method of the type mentioned in the introduction, for ascertaining and/or representing a distribution of scattered radiation produced by the X-ray field, an examination object, which is to be exposed to the X-ray field for imaging, is covered by a covering device, which on the side facing the X-ray tube assembly is embodied to at least partially diffusely reflect the light of the fan of light, and the fan of light facility is activated for emitting a fan of light whose extent matches that of the X-ray field.

The X-ray field may be initially adjusted to the desired extent for the examination by at least one beamforming facility, in particular a collimator and/or a masking facility. If the fan of light facility, which may include a mirror arranged in the beam path of the X-ray radiation in such a way that at least one relevant portion of the at least one beamforming facility acts on the light reflected by the mirror, is now activated, the light of the fan of light, which strikes the covering device, is diffusely reflected and therefore recreates the scattered radiation effect that occurs due to the examination object, in particular a patient, for the X-ray field. Investigations have shown that the scattered radiation distribution of the X-ray radiation is comparable to such a diffuse reflection of light.

Because the covering device expediently adapts at least partially to the shape of the examination object in the covered region, the covering device also maps the shape of the examination object, and this also contributes to the recreation of the behavior of the scattered radiation due to the diffusely reflected light of the fan of light. At least the region of the examination object that faces the X-ray tube assembly is to be covered, in particular in a manner configured to the shape of the region. In particular, the examination object may be completely covered along at least one examination region provided for the imaging, so the examination object is surrounded by the covering device, (e.g., a patient cover or foil). The scattered radiation may then be recreated for any positions of the X-ray tube assembly (not covered by a patient positioning device which is not optically transparent). This is expedient, in particular, with regard to lateral positions of the X-ray tube assembly, in particular to the side of a patient positioned on a patient table, as may occur, for example, when a C-arm is used.

It is therefore proposed that a diffusely reflective examination object covering, in particular patient covering, is used whose scatter properties for light of the fan of light are comparable, in particular, with the scatter properties of the examination object, (e.g., a human body), for X-ray radiation. The scattered radiation in the space of the X-ray facility, which may form part of an angiography system for minimally invasive medical interventions, may consequently be rendered qualitatively visible or detectable without radiation, which is actually dangerous, in particular the X-ray radiation, having to be used.

In certain examples, the fan of light facility may be activated before an examination by the X-ray field when the X-ray tube assembly is switched off. The X-ray facility is indeed, as demonstrated, already adjusted for generation of the X-ray field to the desired extent. The light of the fan of light facility may therefore trigger independently of the X-ray radiation in order to check which distribution of scattered radiation exists before use of the X-ray radiation in order to, for example, appropriately adjust protective measures and/or to appropriately change the X-ray field.

The fan of light facility is therefore used to render the distribution of scattered radiation visible and/or detectable in a harmless manner. No complex calculations are necessary, instead only a suitable covering device for the patient that is diffusely reflective on the side toward the X-ray tube assembly has to be placed over the patient. The use of a covering device is frequently the case with X-ray examinations anyway, for example, to provide a sterile covering. Therefore, if covering this kind are embodied to be diffusely reflective, no additional work step is required; if the diffusely reflective covering device is additionally provided, it is nevertheless easily and quickly placed over the examination object, in particular the patient.

The control facility of the X-ray facility may have a less complex configuration because complex algorithms are no longer necessary for assessing the distribution of scattered radiation.

An advantageous development of the disclosure may provide that the fan of light facility emits visible light. In this case, the scattered radiation is rendered qualitatively visible in the space for humans, so directly illuminated objects or individuals are immediately visible. It is thus possible to intuitively visually assess whether the current measures for scattered radiation protection are adequate, in particular radiation protection facilities are correctly arranged. In this way, an immediately understandable, intuitive visualization of the distribution of scattered radiation is possible without complex calculations, assessment procedures, and the like.

Alternatively, or additionally, sensor data, which describes light of the fan of light reflected by the covering device, may advantageously be recorded by at least one light sensor, which is arranged at a measuring position outside of the X-ray field, and evaluated by an evaluation unit for ascertaining scattered radiation assessment information. An embodiment of this kind may be expedient, in particular, when the light reflected by the covering device, in particular owing to a residual illumination of the space, is too weak for sufficiently clear optical visibility by a human, or also when light outside of the visible spectrum is used. For example, light from the infrared range may be used instead of or in addition to light from the range visible to humans and may be measured by the light sensors. In particular, a wavelength range may be purposefully selected in which there is as little as possible interfering light in the space. In other words, it is expedient to select the wavelength range measured by the at least one light sensor in accordance with the wavelength range of the light of the fan of light.

A measurement is expedient because an objective evaluation of the quantitative distribution of the light of the fan of light reflected by the covering device and thus qualitatively of the distribution of scattered radiation is possible, which may be used, in particular immediately, also for control measures, (e.g., for scattered radiation reduction for regions in which individuals are situated, and/or for scattered radiation protection and/or for warning and/or for informing individuals), as discussed in more detail below. The scattered radiation assessment information therefore describes, in particular, the assessed qualitative distribution of scattered radiation derived from quantitative measurement of the light of the fan of light reflected by the covering device, for which reason a plurality of measuring positions may be used, therefore a plurality of light sensors is used.

In this connection, an optoelectronic sensor and/or a camera may be used as the at least one light sensor. Other types of light sensors, (e.g., simple photo cells), may also be used.

The evaluation unit may be part of a control facility of the X-ray facility. Operation of the fan of light facility and, for example, by a recording unit, of the X-ray tube assembly may also be controlled via the control facility. The recording of the sensor data of the light sensors by the control facility may also be started with activation of the fan of light facility.

In a particularly expedient embodiment, a first light sensor of a light sensor arrangement, which may be worn, in particular hung around the neck, by an individual may be used as at least one of the at least one light sensor. If at least one first light sensor is fixed to an individual, it is possible to check whether relevant scattered radiation strengths are being produced at their position. In particular, a plurality of first light sensors are arranged on an individual. The individual may move when the fan of light facility is switched on in order to check the exposure to scattered radiation at different positions. For example, the at least one first light sensor may be arranged on an individual by a carrier, (e.g., an article of clothing, a lanyard, or the like), of the light sensor arrangement. In exemplary embodiments, an arrangement of first light sensors, which may be positioned over the front torso of the individual, may also be used. A light sensor arrangement that may be worn on the head is also conceivable.

Alternatively, or additionally, a second light sensor may be used as at least one of the at least one light sensor, which is or will be fixed, in particular detachably, at a position provided for the possible attendance of an individual. For example, the second light sensor may include a fixing device or mechanism, for example, for magnetic or another type of adherence to other surfaces. The fixing mechanism may be detachably configured, but alternatively may provide a permanent arrangement of at least one second light sensor, in particular a plurality of second light sensors, at positions where individuals are conventionally situated.

In certain examples, a control unit may check at least one condition for measures, which evaluates the scattered radiation assessment information, on the fulfilment of which at least one of the scattered radiation protective measures and/or scattered radiation reduction measures associated with the condition for measures and/or at least one pointer output measure is executed by the control unit. The control unit may also be part of the control facility of the X-ray facility and also serve other purposes, for example, general actuation of components. Conditions for measures allow an automation of measures on the basis of automatic measuring of the distribution of scattered radiation, in particular also while the fan of light facility and capture of sensor data remains active or when a further activation of the fan of light facility and the measuring may follow automatically. The effect of the measures, in particular the scattered radiation protection and/or scattered radiation reduction measures may thus also be checked.

Specifically, the scattered radiation protection and/or scattered radiation reduction measure may include a positioning of radiation protection equipment, in particular a protective plate, and/or an adjustment of at least one radiation generation parameter of the X-ray tube assembly and/or an adjustment of the extent of the X-ray field. Additionally, or alternatively, the pointer output measure may include the acoustic and/or visual output of a warning and/or the output of a proposal for a procedure for scattered radiation protection and/or for scattered radiation reduction. For example, radiation protection screens are known whose extent, in particular height-wise, may be adjusted, and whose actuating elements may be actuated accordingly. In another specific example, it is conceivable to adjust parameters of the X-ray tube assembly, for example, the tube voltage, a filtering, but also a position and/or orientation of the X-ray tube assembly. Finally, it is also possible to make individuals specifically aware of the current danger by output of a pointer, for example, to output a warning. In addition or alternatively, in particular if an automatic actuation is not possible or not desired, a proposal may be output for a procedure for scattered radiation protection and/or for scattered radiation reduction. This may take place within the meaning of a confirmation request, after which, for components which may be actuated, an automatic implementation of at least one scattered radiation protection and/or scattered radiation reduction measure may take place in accordance with the proposal.

In certain examples, the covering device at least partially has a reflective coating on the side remote from the examination object and/or at least one reflective material is integrated, (e.g., woven), in the covering device. For example, the coating and/or the material may include a metal or a metal alloy. In another embodiment, the coating may include a reflective powder and/or the coating may be introduced into the covering device as the material. It may also be expedient in the case of an at least partially textile covering device to use threads made of, in particular diffusely, reflective material, (e.g., with metal filaments), to produce the covering device or to integrate them therein. It is evident that there is a plurality of variants for designing the covering device to be diffusely reflective, which are basically known for other applications, which may also be used.

An expedient development may provide that the reflective embodiment is implemented by a pattern of diffusely reflective partial areas on the side facing the X-ray tube assembly. In this case, a covering device that, in the region exposed to the fan of light, is embodied to not be completely diffusely reflective but only to the extent that an adequate reflection for adequate visibility and/or for adequate measurability takes place is therefore used as the covering device. In this way, interfering light effects may be avoided in the case of visible light. In addition, even the covering of the X-ray field constituted by the fan of light may remain easily and clearly visible on the examination object.

Specifically, the pattern may be formed from intersecting, diffusely reflective strips, in particular as a rhombic pattern. Other patterns that provide sufficiently good or dense coverage, (e.g., dot patterns, checked patterns, and the like), may also be used.

Different materials may be used in order to achieve the diffuse reflectivity. Suitable materials for achieving diffuse reflection may include barium sulphate, materials based on optical PTFE, ODM98, glass reflector foils, and the like.

A foil and/or a patient cover may be used as the covering device. This connection may provide the diffusely reflective property on a covering device such as a patient cover, which is used anyway, and may be provided at different points or so as to be wrapped around the entire patient in a manner configured to their shape. A different covering device is also possible, e.g., implemented as a foil that proves to be expedient in particular when the patient is to be completely encircled in the examination region (as a section of its length).

In exemplary embodiments, the covering device may be stretched at least partially over the examination object and diffusely reflect the light of the fan of light at a smooth portion of the side facing the X-ray tube assembly. In an embodiment of this kind, diffusely reflective, smooth surfaces may be used, and uneven surfaces do not have to be fashioned in order to produce the diffuse reflection. In particular, the covering device still continues to fit at least roughly, for example, sufficiently closely, the shape of the examination object. For example, the covering device may be laid over the torso of a patient so as to reproduce the approximately elliptical cylindrical shape.

In many cases, the X-ray field is adjusted such that it only strikes the examination object. Not only is the region in which image data is really desired irradiated and scattered radiation reduced from the outset in this way, but excessive differences in contrast, which may impair the image quality, are also avoided. If the situation nevertheless occurs where part of the X-ray field does not strike the examination object and the covering device, it may be provided that even with a region that is remote from the examination object, is not covered by the covering device and is illuminated by the X-ray field a further reflecting device, in particular diffusely reflective in the same way as the covering device, is used for this region. If the material on which part of the X-ray field impinges has different scatter properties, the reflective properties may also be adjusted accordingly.

Apart from the method, the disclosure also relates to an imaging X-ray facility, having an X-ray tube assembly for emitting an X-ray field and a fan of light facility, associated with the X-ray tube assembly, for emitting a fan of light, whose extent matches that of the X-ray field, wherein the X-ray facility also has a covering device for covering an examination object to be examined with the X-ray field, which on the side to be turned toward the X-ray tube assembly at least partially diffusely reflecting the light of the fan of light is reflectively embodied for ascertaining and/or representing a distribution of scattered radiation, which is produced by the X-ray field adjusted in its extent for an examination. All statements with regard to the method may be transferred analogously to the X-ray facility, and vice versa, so the advantages already stated may therefore also be obtained with the X-ray facility.

In particular, the X-ray facility associated with the X-ray tube assembly has at least one beamforming facility for adjusting the extent of the X-ray field. The X-ray tube assembly may form part of a recording arrangement, which also includes an X-ray tube assembly. The recording arrangement may move in respect of at least one degree of freedom, so the X-ray field also changes its position and/or orientation in the space. The fan of light facility and the beamforming facility with the X-ray tube assembly expediently form an X-ray tube assembly arrangement, in particular a structural unit, in this connection which is jointly moved. Such an X-ray tube assembly arrangement may also have at least one filtering facility for optionally introducing at least one filter into the beam path of the X-ray field. In particular, the X-ray facility may have at least one light sensor.

Overall, the X-ray facility may be a radiography facility. The X-ray facility may also be part of an angiography system and may have a C-arm on which the X-ray tube assembly and an or the X-ray detector are arranged opposite each other.

In certain examples, the X-ray facility may have a control facility configured to carry out acts of the method, which are to be automatically carried out. The control facility may include at least one processor and at least one storage device (e.g., memory). The control facility may include functional units formed by software and/or hardware. In particular, apart from a recording unit, the controlling of the recording operation may be performed via one or more of the following: an adjusting unit configured to adjust an extent of the X-ray field, in particular by way of actuation of the beamforming facility; a control unit configured to actuate at least the fan of light facility; and/or an evaluation unit configured to evaluate sensor data of the at least one light sensor.

The control unit may also be configured to evaluate the at least one condition for measures and actuate corresponding components for carrying out the associated measure.

BRIEF DESCRIPTION OF THE DRAWINGS

Further advantages and details of the present disclosure may be found in the embodiments described below and on the basis of the drawings. In the drawings.

DETAILED DESCRIPTION

Figure 1:
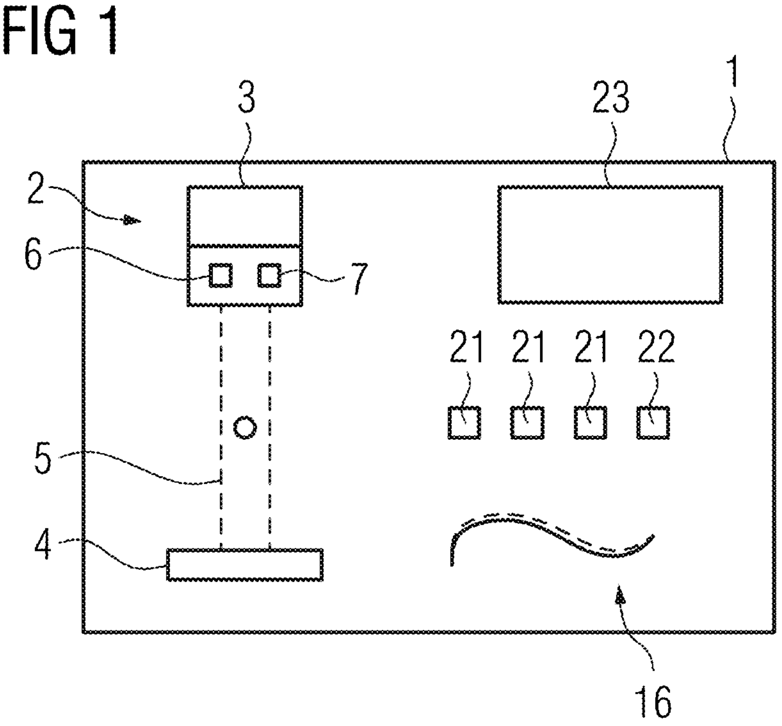
FIG. 1 depicts a schematic diagram of an example of an X-ray facility.

FIG. 1 shows a schematic diagram of an X-ray facility 1. The X-ray facility 1 includes an X-ray tube assembly arrangement 2 with an X-ray tube assembly 3 and an X-ray detector 4. The X-ray tube assembly 3 and the X-ray detector 4 form a recording arrangement that may be arranged on a C-arm 5, indicated only schematically here. The recording arrangement may move in respect of a patient, as the examination object, placed on a patient table (not shown) of the X-ray facility 1.

Apart from the X-ray tube assembly 3, the X-ray tube assembly arrangement 2 also includes at least one beamforming facility 6, (e.g., a collimator and/or a masking facility), as well as a fan of light facility 7. An X-ray field, which is generated by the X-ray tube assembly 3 and is emitted to the X-ray detector 4, may be adjusted in its extent by the beamforming facility 6. The fan of light facility 7 allows a fan of light to be generated whose extent matches the X-ray field and which may thus display the region exposed to the X-rays on the examination object.

Figure 2:
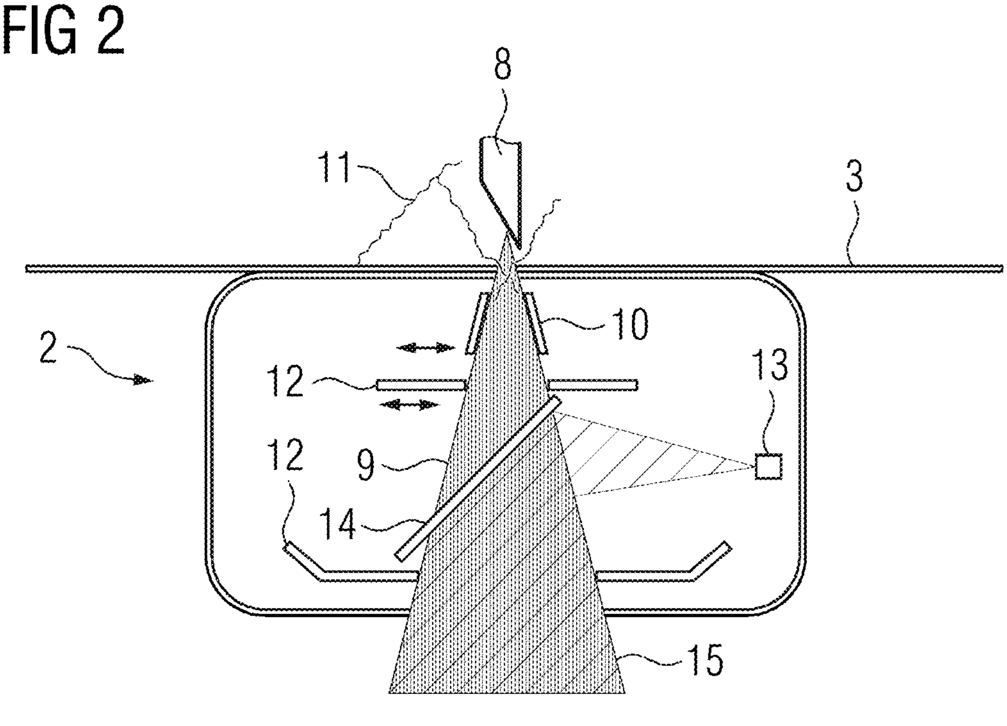
FIG. 2 schematically depicts an example of an X-ray tube assembly arrangement of the X-ray facility.

A specific embodiment is shown for example in FIG. 2. For the sake of clarity, of the X-ray tube assembly 3, which in the present case is embodied as an X-ray tube, only the rotating anode 8, and the X-ray exit window 11 adjacent to it, is shown. The X-rays of the X-ray field 9 exit the X-ray tube assembly 3 through the X-ray exit window 11, it being possible for extrafocal radiation to be absorbed by collimators 10. In the present case, the beamforming facility 6 includes further masks 12, which may move in accordance with the arrows shown. In certain examples, apart from the beamforming facility 6, a filtering facility (not shown in more detail here) may also be provided.

In the present case, the fan of light facility 7 includes a light source 13 arranged in a shared housing with the beamforming facility 6, and an X-ray transparent mirror 14 which is arranged in the X-ray field 9. The light reflected by the mirror 14 in the direction of the X-ray radiation is at least partially also influenced by the beamforming facility 6, so the light exits the X-ray tube assembly arrangement 2 congruently with the X-ray field 9, i.e. to be able to display the extent of the X-ray field 9 as a fan of light 15.

Returning to FIG. 1, the X-ray facility 1 also includes a covering device 16, which at least on one side, which is to be turned toward the X-ray tube assembly 3, at least in a region indicated here by broken lines, is embodied to be diffusely reflective for the light of the fan of light facility 7. The covering device 16 is flexible and may thus adjust to the shape of the examination object, here of the patient, in particular even, for example, for lateral positions of the X-ray tube assembly 3, be wrapped around the patient, i.e., encircle them. The covering device 16 may include a patient cover or a foil that may be provided in addition to the patient cover.

The diffusely reflective embodiment may be brought about in different ways. A foil may be composed entirely from a diffusely reflective material, (e.g., ODM98). On the other hand, coatings may also be used and/or diffusely reflective threads, which may include fibers made of metal or another reflective material, and which may be woven in.

Figure 3:
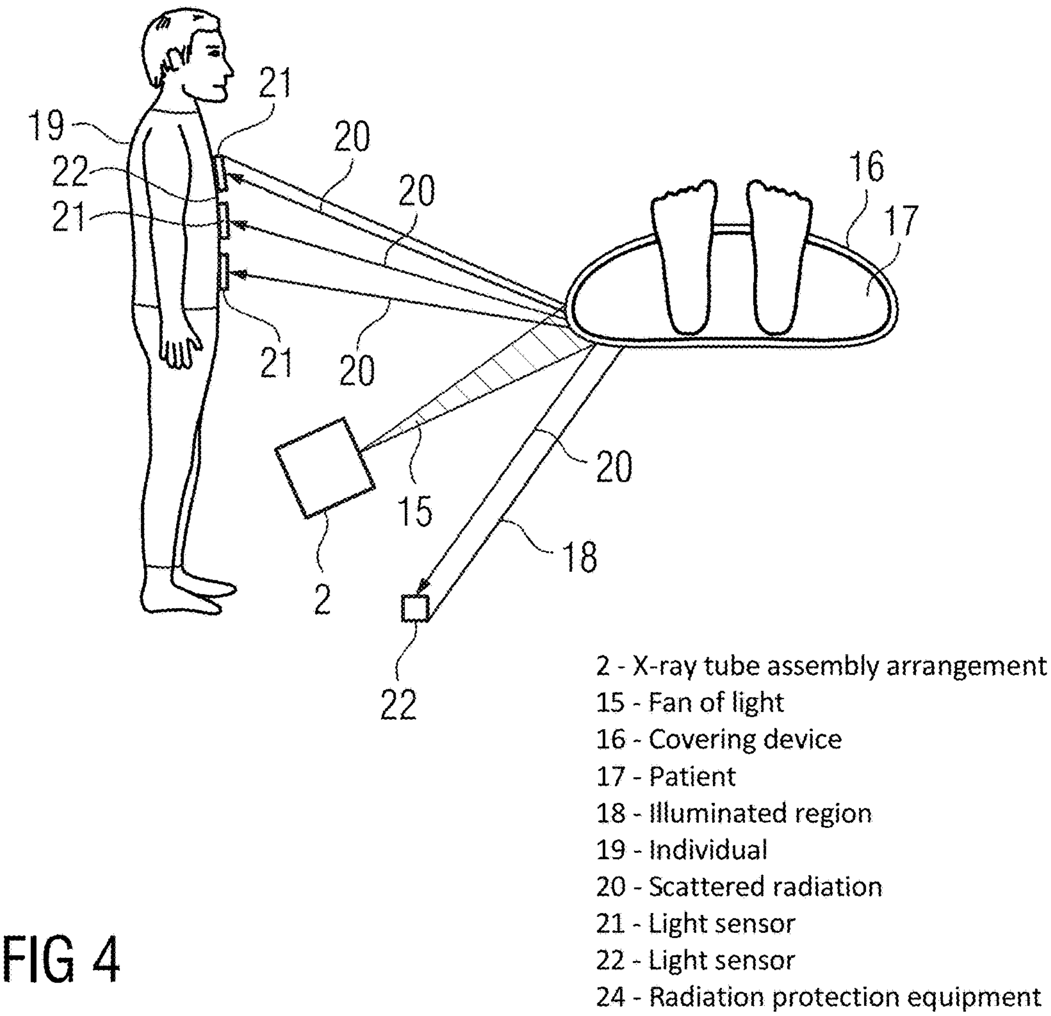
FIG. 3 schematically depicts an example of a functional principle of a covering device.

FIG. 3 explains in more detail the use of the covering device 16 for visualizing and/or ascertaining the distribution of scattered radiation, which may be produced by the X-ray field 9. Schematically shown, there is the examination object, here the patient 17, surrounded by the covering device 16. Starting from the X-ray tube assembly arrangement 2, which is situated here in a lateral position, the fan of light 15, whose extent matches that of the X-ray field 9, is shown. The fan of light facility 7 has already been activated here before use of the X-ray field 9 for imaging, so the fan of light 15 exists independently of any potentially harmful X-ray radiation. When the light of the fan of light 15 strikes the diffusely reflective covering device 16, it is diffusely reflected, and, more precisely, in a manner comparable to the scattered radiation of the X-ray field 9 that occurs due to scattering of the X-rays in the patient 17. The diffusely reflective, illuminated region 18 is schematically indicated.

If the light source 13 generates visible light, the region 18, and thus the distribution of scattered radiation, is visualized.

An individual 19 may therefore establish the extent to which they or other individuals 19 are illuminated, and this applies to objects accordingly.

However, it is also possible to perform a qualitative measurement of the distribution of scattered radiation in that diffusely reflected light of the fan of light 15, schematically indicated here by arrows 20, is measured, for which light sensors 21, 22, also shown in FIG. 1, may be used. In exemplary embodiments, non-visible light, (e.g., infrared light), may also be used for the measurement, and this may be used in addition to or as an alternative to the visible light.

First light sensors 21 are provided for detachable arrangement on an individual 19 and may be part of a light sensor arrangement 22 that may include an article of clothing, a lanyard, or the like, on which the first light sensors 21 are arranged. By the light sensors 21, it is thus possible to measure at different points on an individual 19 whether relevant scattered radiation is to be expected there.

Second light sensors 22, of which only one is shown here, for example, may be fixed, in particular again detachably, at different points in the space in which the X-ray facility 1 is arranged, for example, at points at which individuals 19 may be positioned during an imaging examination. Even if only one second light sensor 22 is shown in the present case, a plurality of second light sensors 22 may expediently be used to record the distribution of scattered radiation as comprehensively as possible. Of course, more than three first light sensors 21 may also be used.

The sensor data of the light sensors 21, 22 may be evaluated by a control facility 23 of the X-ray facility 1 in order to ascertain scattered radiation assessment information describing the distribution of scattered radiation. This may again be evaluated by different conditions for the measures with which measures are associated respectively. Such measures may include scattered radiation protective measures, scattered radiation reduction measures, and/or pointer output measures. Pointer output measures may warn individuals 19 or point out scattered radiation. Scattered radiation reduction measures may lessen scattered radiation, for example, by adjusting radiation generation parameters of the X-ray tube assembly 3.

Figure 4:
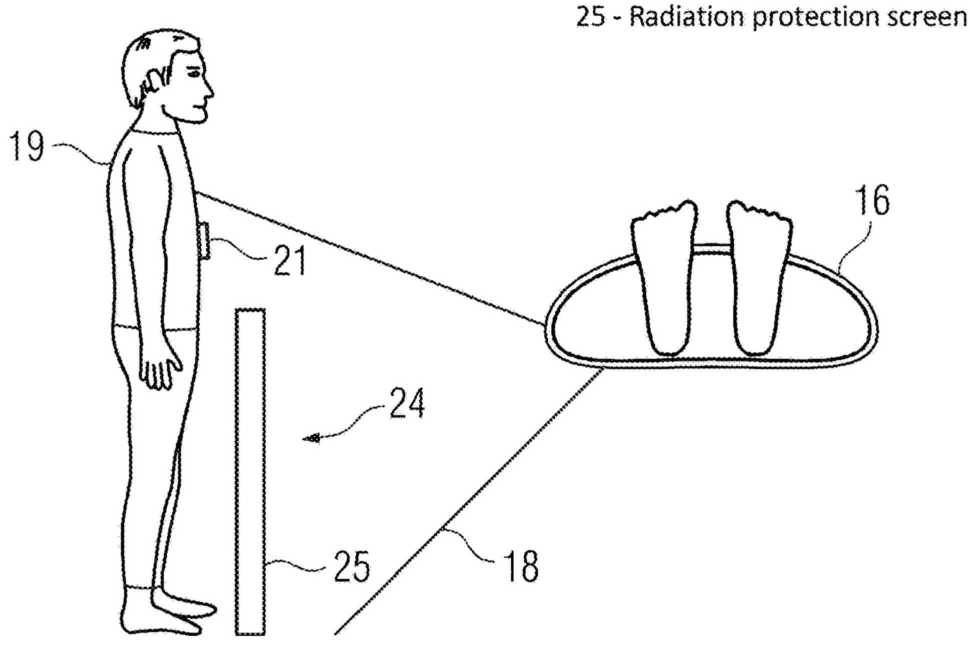
FIG. 4 depicts a schematic sketch of an example of an individual behind radiation protection equipment before a measure has been implemented.
Figure 5:
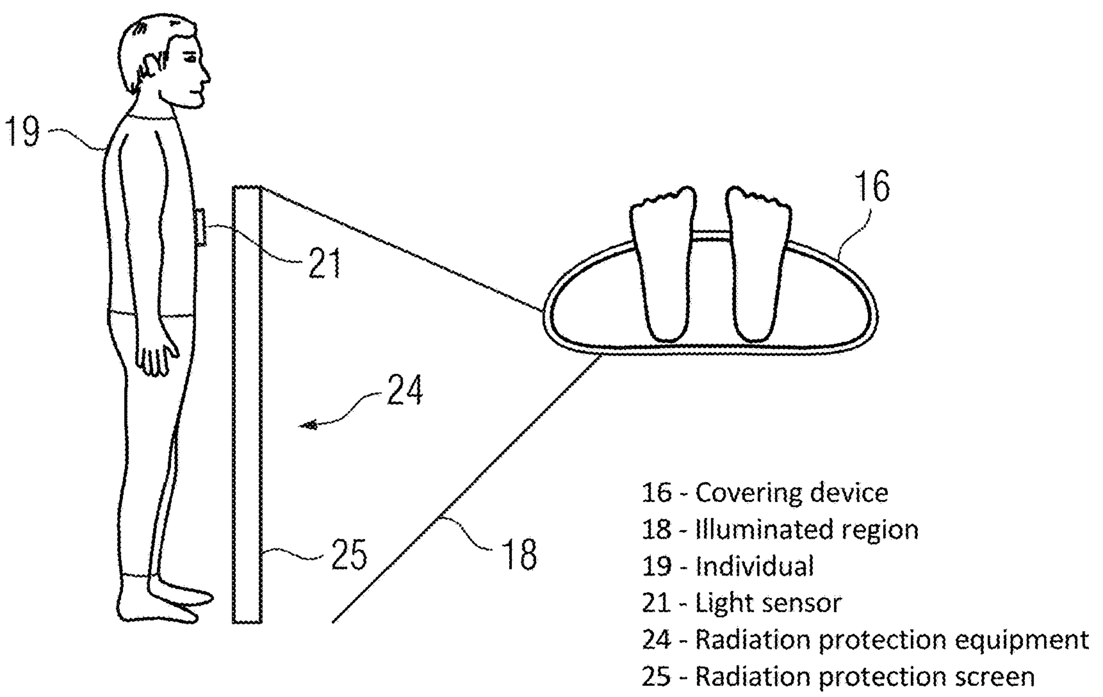
FIG. 5 depicts a schematic sketch of an example an individual behind the radiation protection equipment after the measure has been implemented.

One example of a scattered radiation protective measure is explained in more detail by FIGS. 4 and 5. FIG. 4 shows the situation before the measure has been implemented. An individual 19 is situated partially covered by radiation protection equipment 24, here a radiation protection screen 25, to the side of the patient 17. Nevertheless, the region 18 extends beyond the upper end of the radiation protection screen 25, so a first light sensor 21 measures light on the individual 19 and relevant scattered radiation qualitatively exists there in accordance with the scattered radiation assessment information. A condition for measures is fulfilled, with which, as a scattered radiation protective measure, increasing the radiation protection screen 25, which may be actuated accordingly, is associated.

FIG. 5 shows the situation after this measure has been implemented by the control facility 23. The radiation protection screen 25 is now higher and covers the whole region 18 in respect of the individual 19, so the first light sensor 21 accordingly does not measure light anymore. Further measures are no longer necessary before the X-ray radiation of the X-ray field 9 may actually be triggered for the imaging examination.

Figure 6:
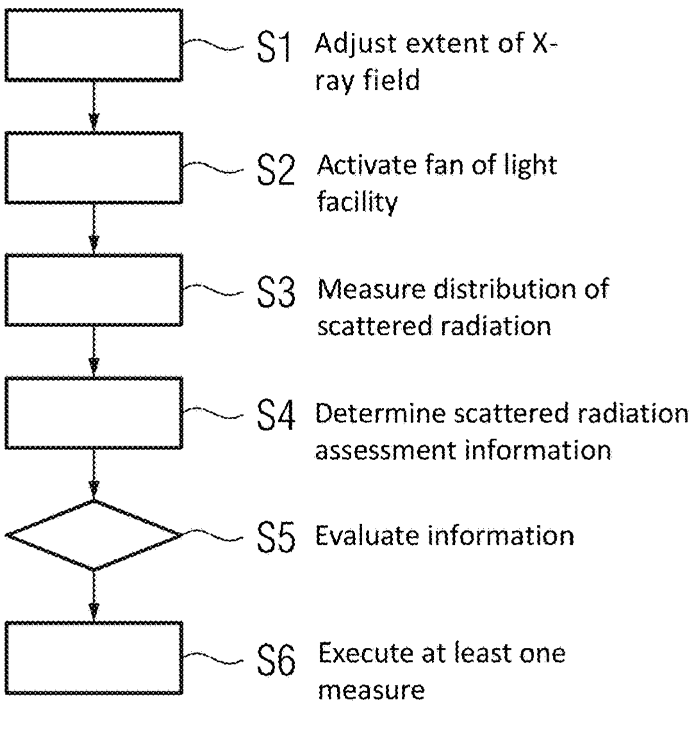
FIG. 6 depicts a flowchart of an example of a method.

FIG. 6 shows a flowchart of an exemplary embodiment of the method in which such a measurement likewise takes place. In act S1, in particular by way of actuation of the beamforming facility 6 by the control facility 23, the desired extent of the X-ray field 9 is adjusted, (e.g., while already using the fan of light 15). The covering device 16 may be arranged on the patient 17 already or be subsequently arranged on them.

Before the X-ray radiation of the X-ray field 9 is actually output, the fan of light facility 7 is activated, in act S2, by the control facility 23. In act S3, the distribution of scattered radiation may therefore be qualitatively measured in the form of the diffusely reflected light of the fan of light 15 using the light sensors 21, 22.

In act S4, the scattered radiation assessment information is accordingly determined from the sensor data of the light sensors 21, 22 in the control facility 23. This information may be evaluated in act S5 by the condition for measures. If at least one condition for measures is fulfilled, the corresponding, associated, at least one measure is executed in act S6.

Figure 7:
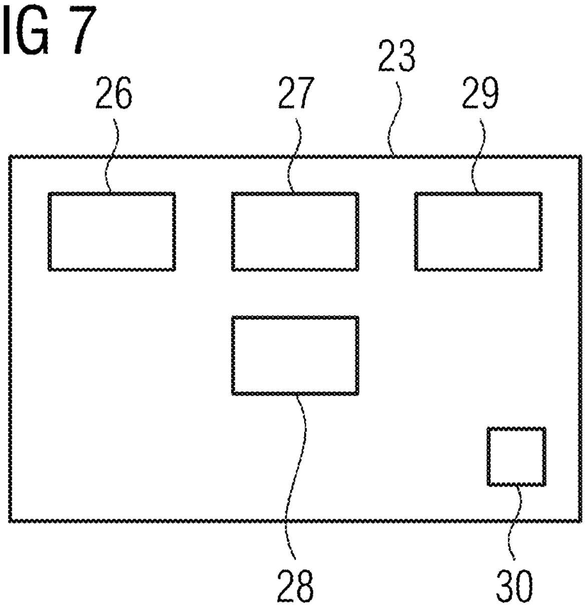
FIG. 7 depicts an example of the functional structure of a control facility of the X-ray facility.

As already mentioned, the control facility 23 controls the operation of the X-ray facility 1. The control facility 23 may also carry out the method, insofar as it may be automated. FIG. 7 shows the functional structure of the control facility 23 in this regard.

Apart from a storage device 30 and a recording unit 26 for controlling the recording operation per se, the control facility has an adjusting unit 27 for adjusting an extent of the X-ray field 9 in accordance with act S1. Further, a control unit 28 is provided, which is embodied for actuating at least the fan of light facility 7, for example, in order to activate it in accordance with act S2. The light sensors 21, 22 may consequently also be actuated accordingly by the control unit 28 for measuring. The sensor data of the light sensors 21, 22 may then be evaluated in an evaluation unit 29 in accordance with act S4. The condition for measures in accordance with act S5 may then again be evaluated by the control unit 28, which actuates corresponding components of the X-ray facility 1 for carrying out the associated measures on fulfilment of the condition.

Figure 8:
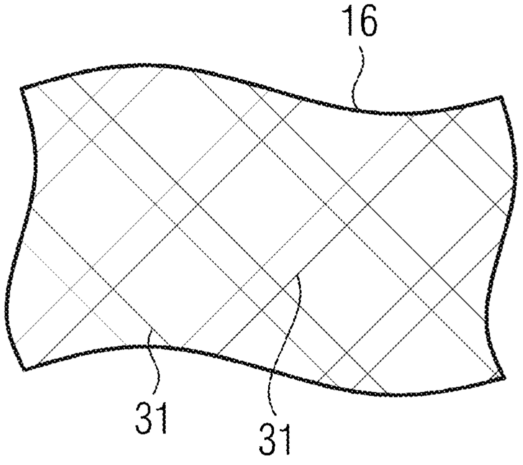
FIG. 8 depicts an example of one possible diffusely reflective pattern on a covering device.

FIG. 8 shows an exemplary embodiment in which the side to be turned toward the X-ray tube assembly 2 is embodied to not be completely diffusely reflective and instead a pattern of diffusely reflective partial areas 31, here strips, is formed in the present case, for example, a rhombic pattern.

It should also be noted that, in particular, when the situation may occur where part of the X-ray field 9 does not strike the examination object (and also the covering device 16), a further reflecting device may also be used.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an imaging X-ray facility having an X-ray tube assembly for emitting an X-ray field, with which a fan of light facility for emitting a fan of light, whose extent matches that of the X-ray field, is associated, the method comprising:

covering, by a covering device, an examination object to be exposed to the X-ray field for imaging, for ascertaining and/or representing a distribution of scattered radiation produced by the X-ray field;

activating the fan of light facility, wherein the covering device at least partially diffusely reflects light of the fan of light on a side of the covering device facing the X-ray tube assembly;

recording sensor data by at least one light sensor of a light sensor arrangement that is arranged at a measuring position outside of the X-ray field, wherein the sensor data describes the light of the fan of light reflected by the covering device; and ascertaining scattered radiation assessment information by evaluating the sensor data by an evaluation unit.

2. The method of claim 1, wherein the fan of light facility is activated before an examination by the X-ray field when the X-ray tube assembly is switched off.

3. The method of claim 1, wherein the fan of light facility emits visible light.

4. The method of claim 1, wherein a first light sensor of a light sensor arrangement worn by an individual is used as a light sensor of the at least one light sensor.

5. The method of claim 4, wherein the first light sensor is hung around a neck of the individual.

6. The method of claim 4, wherein a second light sensor of the light sensor arrangement is further used as an additional light sensor of the at least one light sensor, and wherein the second light sensor is configured to be detachably fixed at a position provided for possible attendance of the individual.

7. The method of claim 1, further comprising:

checking, by a control unit, at least one condition for measures, which the scattered radiation assessment information evaluates, on a fulfilment of which at least one of scattered radiation protective measures and/or scattered radiation reduction measures associated with the condition for measures; and/or executing, by the control unit, at least one pointer output measure.

8. The method of claim 7, wherein the scattered radiation protective measures and/or the scattered radiation reduction measures comprise a positioning of radiation protection equipment, an adjustment of at least one radiation generation parameter of the X-ray tube assembly, an adjustment of the extent of the X-ray field, or a combination thereof, and/or wherein the pointer output measure comprises an acoustic output of a warning, a visual output of the warning, an output of a proposal for a procedure for scattered radiation protection, an output of a proposal for a procedure for scattered radiation reduction, or a combination thereof.

9. The method of claim 8, wherein the radiation protection equipment comprises a protective plate.

10. The method of claim 1, wherein the covering device comprises a reflective coating at least partially on a side remote from the examination object, and/or wherein the covering device comprises at least one reflective material that is integrated in the covering device.

11. The method of claim 10, wherein the at least one reflective material is woven in the covering device.

12. The method of claim 1, wherein the covering device comprises a pattern of diffusely reflective partial areas on the side of the covering device facing the X-ray tube assembly.

13. The method of claim 1, wherein the covering device comprises a foil and/or a patient cover.

14. The method of claim 1, wherein the covering device is at least partially stretched over the examination object and at least partially diffusely reflects the light of the fan of light at a smooth portion of the side of the covering device facing the X-ray tube assembly.

15. The method of claim 1, further comprising:

covering, by a diffusely reflective device, a region distant from the examination object that is illuminated by the X-ray field and not covered by the covering device, for the ascertaining and/or the representing of the distribution of scattered radiation produced by the X-ray field.

16. The method of claim 15, wherein the region is covered by the diffusely reflective device in a same manner as the covering device.

17. An imaging X-ray facility comprising:

an X-ray tube assembly configured to emit an X-ray field;

a fan of light facility associated with the X-ray tube assembly, wherein the fan of light facility is configured to emit a fan of light whose extent matches that of the X-ray field;

a covering device configured to cover an examination object to be examined with the X-ray field;

at least one light sensor arranged at a measuring position outside of the X-ray field; and an evaluation unit, wherein a side of the covering device facing the X-ray tube assembly is configured to at least partially diffusely reflect light of the fan of light, wherein the covering device is configured to ascertain and/or represent a distribution of scattered radiation produced by the X-ray field, wherein the at least one light sensor is configured to record sensor data, wherein the sensor data describes the light of the fan of light reflected by the covering device, and wherein the evaluation unit is configured to ascertain scattered radiation assessment information by evaluating the sensor data.

* * * * *